(12) United States Patent
Devaux et al.

(10) Patent No.: US 8,735,631 B2
(45) Date of Patent: May 27, 2014

(54) METHOD FOR MANUFACTURING METHYLMERCAPTOPROPIONALDEHYDE AND METHIONINE USING RENEWABLE RAW MATERIALS

(75) Inventors: Jean-François Devaux, Soucleu en Jarrest (FR); Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/128,927

(22) PCT Filed: Nov. 19, 2009

(86) PCT No.: PCT/FR2009/052220
§ 371 (c)(1),
(2), (4) Date: May 24, 2011

(87) PCT Pub. No.: WO2010/058129
PCT Pub. Date: May 27, 2010

(65) Prior Publication Data
US 2011/0229626 A1    Sep. 22, 2011

(30) Foreign Application Priority Data
Nov. 20, 2008 (FR) ...................... 08 57886

(51) Int. Cl.
C07C 319/14 (2006.01)
C07C 323/22 (2006.01)
C07C 323/58 (2006.01)
A23K 1/16 (2006.01)

(52) U.S. Cl.
USPC .............. 568/41; 562/559; 426/648

(58) Field of Classification Search
USPC .............. 426/648; 568/41; 562/559
See application file for complete search history.

(56) References Cited

U.S. PATENT DOCUMENTS

| | | | |
|---|---|---|---|
| 2,745,745 A | 5/1956 | Blake et al. | |
| 3,433,840 A | 3/1969 | Shima et al. | |
| 3,529,940 A | 9/1970 | Shima et al. | |
| 4,225,516 A * | 9/1980 | Biola et al. ............ | 568/41 |
| 4,943,662 A | 7/1990 | Arretz | |
| 5,387,720 A | 2/1995 | Neher et al. | |
| 5,637,766 A * | 6/1997 | Hsu et al. ............ | 562/512 |
| 5,770,021 A | 6/1998 | Hego et al. | |
| 5,770,769 A | 6/1998 | Geiger et al. | |
| 5,990,349 A | 11/1999 | Geiger et al. | |
| 2004/0055716 A1 | 3/2004 | Landalv et al. | |
| 2006/0183945 A1 | 8/2006 | Redlingshofer et al. | |
| 2008/0018319 A1 | 1/2008 | Chang et al. | |
| 2008/0119663 A1 | 5/2008 | Redlingshoefer et al. | |
| 2008/0183019 A1 | 7/2008 | Redlingshofer et al. | |

FOREIGN PATENT DOCUMENTS

| | | |
|---|---|---|
| EP | 0142488 A2 | 5/1985 |
| EP | 0333527 A1 | 9/1989 |
| EP | 0751110 A1 | 1/1997 |
| EP | 0889029 A2 | 1/1999 |
| EP | 1300384 A2 | 4/2003 |
| EP | 1408029 A1 | 4/2004 |
| EP | 1408029 B1 | 11/2006 |
| EP | 1556343 B1 | 8/2007 |
| EP | 1978009 A1 | 10/2008 |
| FR | 1.520.328 | 4/1968 |
| FR | 1.526.335 | 5/1968 |
| FR | 1526355 A | 5/1968 |
| FR | 2 314 917 A1 | 1/1977 |
| FR | 2 477 538 A2 | 9/1981 |
| FR | 2 544 758 A1 | 10/1984 |
| GB | 718112 | 11/1954 |
| GB | 913836 | 12/1962 |
| WO | 9410085 A1 | 5/1994 |
| WO | 9429254 A1 | 12/1994 |
| WO | 9640631 A1 | 12/1996 |
| WO | 9700858 A1 | 1/1997 |
| WO | 9736848 A1 | 10/1997 |
| WO | 03068721 A1 | 8/2003 |
| WO | 2006087083 A2 | 8/2006 |
| WO | 2006087084 A2 | 8/2006 |
| WO | 2008002053 A1 | 1/2008 |

OTHER PUBLICATIONS 3-(Methylthio) priopionaldehyde. Available online at www.inchem.org on 2003.*
International Search Report received in PCT/FR2009/052220, mailed Jun. 6, 2010.

* cited by examiner

*Primary Examiner* — Sikarl Witherspoon
(74) *Attorney, Agent, or Firm* — Smith, Gambrell & Russell, LLP

(57) ABSTRACT

The present invention relates to a method for manufacturing methylmercaptopropionaldehyde (MMP) including at least the following steps: (a) dehydrating glycerol to acrolein from an aqueous solution of glycerol in the presence of an acid catalyst; (b) purifying the aqueous flux from step (a) to obtain a flux of acrolein containing at least 15 wt % of water relative to the acrolein; (c) causing a reaction of the acrolein flux obtained in step (b) with methylmercaptan in the presence of a catalyst; (d) optionally purifying the product obtained in step (c). The method of the invention can also include a reaction of the product obtained in step (c) or (d) with hydrocyanic acid, or sodium cyanide during a step (e) followed by a subsequent transformation to produce methionine or methionine hydroxyanalogue, which can then optionally be purified. The additional use of methylmercaptan and/or hydrocyanic acid derived from biomass as raw materials in the method according to the invention makes it possible to obtain MMP, methionine or methionine hydroxyanalogue made up of 100% organic carbon from renewable sources.

17 Claims, No Drawings

METHOD FOR MANUFACTURING METHYLMERCAPTOPROPIONALDEHYDE AND METHIONINE USING RENEWABLE RAW MATERIALS

FIELD OF THE INVENTION

The present invention relates to the production of methionine and to a synthetic protein used as an animal feed supplement, from a renewable starting material. More precisely, the invention relates to an industrial process for producing methylmercaptopropionaldehyde, which is a key intermediate for the synthesis of methionine, and methionine from renewable starting materials.

Methionine, or 2-amino-4-(methylthio)butyric acid, of chemical formula $H_3C—S—(CH_2)_2—CH(NH_2)—COOH$, is an essential amino acid, not synthesized by animals, necessary as an addition in the food ration, especially that of poultry, whose methionine requirements are great. Methionine obtained via chemical synthesis has become established as a substitute for supplies of natural origin (fish meal, soybean meal, etc.) for animal feed. The main market is that of poultry feed.

In contrast with the other amino acids, methionine is biologically assimilable both in the dextrorotatory form (d or +) and in the laevorotatory form (l or −), which has allowed the development of chemical syntheses leading to the racemic product. Thus, the synthetic methionine market is mainly that of dl-methionine, a solid product commonly referred to as DLM. A liquid derivative of methionine also exists, the α-hydroxy acid, corresponding to 2-hydroxy-4-(methylthio)butyric acid of chemical formula $H_3C—S—(CH_2)_2—CH(OH)—COOH$, which has the particular property of being converted in vivo into methionine virtually quantitatively. This liquid product, which is commercially available in the form of an aqueous solution at 88% by mass, is commonly referred to as the hydroxy analogue of methionine.

Numerous syntheses relating to methionine or to its hydroxylated derivative have been described, but the chemical processes exploited industrially are essentially based on the same main starting materials and the same key intermediate products, namely:

acrolein $H_2C=CH—CHO$ and methyl mercaptan $H_3CSH$ (MSH) leading via reaction to methylmercaptopropionaldehyde $H_3C—S—CH_2—CH_2—CHO$ (MMP), also known as 3-(methylthio)propanal or methylthiopropionic aldehyde (MTPA), hydrogen cyanide (HCN) or sodium cyanide (NaCN), which, after reaction with MMP, leads finally to methionine or to the hydroxy analogue of methionine.

Reference may be made to the article in Techniques de l'Ingénieur, traité Génie des Procédés, J 6-410-1 to 9, which describes the conditions for the industrial implementation of processes for synthesizing methionine passing via methylmercapto-propionaldehyde as intermediate product.

Acrolein, which is used as a starting material for producing methylmercaptopropionaldehyde, is mainly obtained by gas-phase atmospheric oxidation of propylene over a catalyst based on bismuth molybdate at about 350° C.

The hydrogen cyanide used to produce the methionine is obtained by reacting ammonia with methane, methanol or a hydrocarbon such as propane or propylene, optionally in the presence of air and/or oxygen.

As a result, the methylmercaptopropionaldehyde and consequently the methionine are synthetic products that are strongly dependent on starting materials of fossil or petroleum origin which contribute towards increasing the greenhouse effect. Specifically, propylene is obtained by the catalytic cracking or vapour cracking of petroleum fractions. Ammonia is obtained by reacting atmospheric nitrogen and hydrogen obtained from the steam reforming of hydrocarbons present in naphtha or in natural gases. Methane is the main component of natural gas, a fossil fuel formed from a mixture of hydrocarbons naturally present in porous rocks in gaseous form. Propane is extracted either from crude petroleum during refining operations or from natural gas and associated gases in oil fields.

Given the worldwide decrease in petroleum reserves, the source of these starting materials will gradually diminish. Starting materials of plant or animal origin are renewable sources and have a reduced impact on the environment. They do not require all the refining steps (very energy intensive) of petroleum-derived products. They contribute all the less to climatic warming since atmospheric $CO_2$ is consumed by photosynthesis during their biosynthesis.

It thus appears necessary to have available synthetic processes that are not dependent on starting materials of fossil origin, but rather that use starting materials of renewable origin.

The aim of the present invention is thus to provide a process for synthesizing methylmercaptopropionaldehyde and a process for synthesizing methionine based on the use of renewable starting materials. In particular, the acrolein included as starting material in these processes may be obtained as a product of dehydration of glycerol, which is itself derived from the methanolysis of plant oils at the same time as the methyl esters, which are used especially as fuels or combustibles in diesel and domestic fuel oil.

The process according to the invention thus makes it possible to dispense with the consumption of petroleum, to reduce the energy consumption and to make use of natural products that are available in large amount.

PRIOR ART

It has been known for a long time that glycerol can lead to the production of acrolein.

U.S. Pat. No. 5,387,720 describes a process for producing acrolein by dehydration of glycerol, in the liquid phase or in the gas phase, on acidic solid catalysts defined by their Hammett acidity. According to the authors of the said patent, the gas-phase reaction is preferable since it makes it possible to obtain a degree of conversion of glycerol of close to 100%. However, it leads to an aqueous acrolein solution containing side products, such as hydroxypropanone, in large amount.

Patent applications WO 2006/087 084 and WO 2006/087 083 propose improvements to this process by choosing very acidic catalysts, or by introducing oxygen during the glycerol dehydration reaction. Propionaldehyde and acetaldehyde are co-produced in large amount in these processes.

Patent application US 2008/0 119 663 describes the preparation of acrolein from triglycerides, the aqueous acrolein solution obtained being able to be used as starting material for the preparation of methionine.

None of these documents describes how to purify the acrolein produced in order directly to feed a unit for producing methylmercaptopropionaldehyde by reaction with methyl mercaptan, or to feed a unit for producing methionine.

The reaction between acrolein and methyl mercaptan (MSH) to form methylmercaptopropionaldehyde (MMP) may be performed in the liquid phase, after production, purification and isolation in liquid form of the acrolein. The reaction is generally performed in the presence of a basic catalyst, in the absence of solvent, at about 40-50° C., with a slight excess of MSH. The acrolein used is generally commercial acrolein containing a few % of water. The catalysts that may be used for the liquid-phase reaction are, for example, organic bases, optionally combined with an organic acid. Examples that may be mentioned include organic bases selected from amines such as those described in patent application WO 1996/40631, organic bases of N-alkylmorpholine type described in document EP 1 556 343, or systems formed from a basic compound and an acidic compound in mole ratios of less than 0.3/1 described in document EP 1 408 029. The most conventional catalyst is pyridine combined with acetic acid. The yields are virtually quantitative. The MMP obtained is then purified by distillation. Light impurities and heavy sulfurous products are thus separated out, and then incinerated.

Many documents describe processes for performing the reaction between liquid acrolein and methyl mercaptan. Mention may be made of document FR 1 526 355, which describes the synthesis of MMP by reacting MSH with an aqueous acrolein solution containing at least one carbonyl compound chosen from saturated aliphatic aldehydes and saturated aliphatic ketones but free of unsaturated organic acids. The aqueous acrolein solution is obtained from propylene or by condensation of formaldehyde with acetaldehyde, and partial purification by elimination of the components with a boiling point higher than that of acrolein. The by-products present in the acrolein solution, mainly acetaldehyde, propionaldehyde and acetone, must then be separated out during the purification of MMP after reaction with MSH.

In document FR 1 520 328, it has been proposed to perform the synthesis of MMP from acrolein in two steps, consisting in placing MSH in contact with MMP until the evolution of the heat produced is complete, and then in placing the resulting reaction product in contact with acrolein. This process allows efficient control of the reaction temperature.

MMP may also be obtained by direct synthesis via reaction of methyl mercaptan with the acrolein-containing gaseous effluent originating from the catalytic oxidation of propylene, after partial purification of this stream, using MMP itself both as the acrolein-absorbing solvent and as the reagent with MSH (FR 2 314 917, EP 022 697, EP 889 029, WO 94/29254, WO 97/00858).

In documents FR 2 314 917 and EP 022 697, the gaseous mixture containing acrolein is freed of the acrylic acid and water it contains by condensation at low temperature, before reaction with methyl mercaptan. Absorption with MMP of the gas stream thus purified may be performed prior to the reaction with methyl mercaptan.

In documents WO 94/29254 and WO 97/00858, the gaseous effluent containing acrolein, steam and uncondensable gases is placed in contact with a reaction medium containing MMP, methyl mercaptan and a catalyst for the reaction between acrolein and methyl mercaptan, to form a liquid reaction product containing MMP. The mole ratio between the steam and the acrolein present in the gaseous effluent is preferably less than 0.3. The uncondensable gases including oxygen, nitrogen, carbon monoxide and carbon dioxide are present in the gaseous effluent in a proportion that may be from 60% to 80%, and must then be separated from the liquid reaction product. This process has the drawback of sending a large stream of uncondensable gases into the reaction medium, which may lead to a loss of methyl mercaptan from this medium during their separation and generate a stream of uncondensables polluted with sulfur compounds.

In document WO 97/36848, the gaseous acrolein stream, derived from a reaction of propylene with oxygen in the presence of propane as diluent, is partially condensed to give an acrolein stream containing acetaldehyde in a content of between 0.5% and 3.5% by weight and water in a content of between 2% and 8%. This acrolein stream, after reaction with methyl mercaptan, leads to MMP comprising a high content of acetaldehyde, which must then be separated out by distillation.

Moreover, processes have been proposed for treating and purifying a gaseous stream containing acrolein derived from the oxidation of propylene, with a view to using it in a reaction for synthesizing MMP. Mention may be made, for example, of document EP 751 110, which describes a process for purifying a gaseous mixture comprising acrolein, water, acids (acrylic acid, formic acid, acetic acid, maleic acid) and uncondensables ($N_2$, $O_2$, other gases of air, CO, $CO_2$, propylene), this process minimizing the risks of degradation of the acrolein while at the same time avoiding fouling of the apparatus used in the process. This process is based essentially on a low-temperature condensation of water and of the majority of the acids present in the stream, and stripping of the condensed aqueous phases to recover the purified acrolein. A purified gaseous fraction containing acrolein and uncondensables whose weight content of water is less than 2% and whose weight content of acids is less than 100 ppm is obtained. However, this technical solution has the drawback of providing a gaseous acrolein stream containing uncondensable gases in large amount, which, after reaction with methyl mercaptan, leads to a large stream of uncondensable compounds polluted with sulfur compounds. Purification of the MMP produced may then prove to be difficult.

Fully integrated processes for synthesizing MMP starting with propylene also exist, without isolation of the intermediate acrolein, which reduces the risks associated with the storage and handling of acrolein. However, these processes require various steps for absorbing and stripping the gaseous stream derived from the oxidation of propylene. In document WO 03/068 721, the uncondensable gases present in the crude product of catalytic oxidation of propylene are separated out upstream of the reaction with methyl mercaptan, and can thus be recycled into the propylene oxidation, without having been polluted by any sulfur products generated by the methyl mercaptan or the MMP. The gaseous acrolein stream derived from the absorption and stripping steps contains water, but may be used directly in gaseous form for the synthesis of MMP. However, this process remains dependent on a starting material of fossil origin.

More recently, patent application US 2006/0 183 945 describes the direct synthesis of MMP from glycerol. The process consists in placing glycerol in contact with methyl mercaptan, in the liquid phase or in the gas phase, in the presence of an acidic solid catalyst and optionally of a solvent. The liquid-phase reaction is performed at a temperature of between 50° C. and 500° C. at a pressure ranging from 1 to 300 bar and with a solvent or diluent such as water, an alcohol, acetone, toluene, or MMP itself. The glycerol concentration is from 1% to 100% and preferably from 5% to 40% relative to the solvent or diluent. The mole ratio between the glycerol and the MSH is adjusted to between 0.2 and 50 and preferably between 0.8 and 10. When the synthesis is performed in the gas phase, the reaction temperature is between 200° C. and 550° C. and in particular between 250° C. and 350° C., at a pressure ranging from 1 to 100 bar and preferably from 1 to 30 bar. The gaseous mixture may be diluted, for example with nitrogen, air or steam. The catalysts that may be used are acidic heterogeneous catalysts with a Hammett acidity of less than +2 and preferably less than −3. It is possible for the methyl mercaptan not to be added immediately at the start of the reaction, but after partial conversion of the glycerol under the reaction implementation conditions. The process is performed in batch or semi-continuous mode with continuous introduction of methyl mercaptan, in a single-zone reactor, or in a reactor with two reaction zones. The MMP yields obtained using this process are, according to the examples, 29 mol % and 4 mol % relative to the glycerol. These yields are insufficient to envisage an industrial production of MMP on the basis of this process. Moreover, such yields would oblige an overconsumption of energy and would considerably reduce the environmental interest of a production process using a renewable starting material.

Patent application US 2008/0 183 019 also describes a process for producing MMP from glycerol and MSH directly in a single step using a catalyst with a Hammett acidity of less than +2 and which comprises tungsten and one or more promoters. The fact of performing the process in a single step makes it necessary to perform the reaction in temperature zones in which the MMP is sparingly stable, which greatly limits the yields.

As regards methionine, it is obtained by reacting MMP either with sodium cyanide (NaCN) in the presence of $CO_2$ and $NH_3$, followed by saponification with a strong base of the aqueous hydantoin solution formed and then acidification (Bücherer synthesis), or with hydrogen cyanide (HCN) to form the intermediate cyanohydrin, which is then converted into the aminonitrile and then hydrolysed to methionine (Strecker synthesis).

A variant of these processes lies in the synthesis of the intermediate hydantoin from MMP and HCN, followed by saponification with potassium carbonate and acidification (Degussa process), described, for example, in U.S. Pat. No. 5,990,349.

The synthesis of the hydroxy analogue of methionine also proceeds via synthesis of the intermediate cyanohydrin, which is then hydrolysed in two steps, the first step being performed at low temperature to form the amide, the second step at a higher temperature leading to the desired product in the absence of heavy by-products.

Mention may be made of the following documents: U.S. Pat. No. 2,745,745; EP 142 488 and EP 333 527, which describe processes for producing the hydroxy analogue of methionine.

More recently, international patent application WO 2008/002 053 proposes a process for producing amino acids, for instance methionine, by fermentation of glycerol.

SUMMARY OF THE INVENTION

The Applicant Company has now found a process for manufacturing methylmercaptopropionaldehyde by addition of methyl mercaptan to acrolein, characterized in that at least one from among the acrolein and the methyl mercaptan employed in this reaction is obtained via a reaction or a sequence of reactions starting from biomass.

A subject of the invention is also a process for manufacturing methionine or the hydroxy analogue of methionine by reacting hydrogen cyanide or the sodium salt of hydrogen cyanide with methylmercaptopropionaldehyde, the methylmercaptopropionaldehyde having been obtained by adding methyl mercaptan to acrolein, characterized in that at least one from among the acrolein, the methyl mercaptan and the hydrogen cyanide employed is obtained via a reaction or a sequence of reactions starting from biomass.

The invention has the effect of reducing global warming during the manufacture of MMP and methionine, by reducing the emissions of greenhouse gases associated with their manufacture. Moreover, the use of renewable starting materials for all of the compounds employed in the processes according to the invention will make it possible to consolidate the "green" nature of these processes, the products obtained, MMP and methionine then possibly being 100% formed from organic carbon derived from renewable resources.

A subject of the invention is also a process for manufacturing methylmercaptopropionaldehyde, comprising at least the following steps:
(a) dehydration of glycerol to acrolein starting with an aqueous glycerol solution in the presence of an acidic catalyst,
(b) purification of the aqueous stream derived from step (a) to obtain an acrolein stream containing less than 15%, preferably less than 7% and more preferably less than 4% by mass of water relative to the acrolein,
(c) reaction of the acrolein stream obtained in step (b) with methyl mercaptan in the presence of a catalyst,
(d) optionally, purification of the product obtained in step (c).

The said process according to the invention leads to high yields, and makes it possible to overcome the drawbacks of the abovementioned current processes.

A subject of the invention is also a process for manufacturing methionine or the hydroxy analogue of methionine, comprising at least the following steps:
(a) dehydration of glycerol to acrolein starting with an aqueous glycerol solution in the presence of an acidic catalyst,
(b) purification of the aqueous stream obtained derived from step (a) to obtain an acrolein stream containing less than 15%, preferably less than 7% and more preferably less than 4% by mass of water relative to the acrolein,
(c) reaction of the acrolein stream obtained in step (b) with methyl mercaptan in the presence of a catalyst,
(d) optionally, purification of the product obtained in step (c),
(e) reaction of the product obtained in step (c) or (d) with hydrogen cyanide or sodium cyanide,
(f) conversion of the product obtained in (e) into methionine or the hydroxy analogue of methionine, and purification thereof.

DETAILED DESCRIPTION OF THE INVENTION

The invention uses biomass as starting material. The term "biomass" means naturally produced starting material of plant or animal origin. This plant material is characterized in that the plant, for its growth, has consumed atmospheric $CO_2$ while at the same time producing oxygen. Animals, for their growth, have, for their part, consumed this plant starting material and have thus assimilated the carbon derived from atmospheric $CO_2$.

The present invention thus addresses certain durable development concerns, by obtaining methylmercaptopropionaldehyde and methionine for which at least part of their carbon originates from renewable sources.

A renewable starting material is a natural animal or plant resource whose stocks can be reconstituted over a short period on a human timescale. It is in particular necessary for this stock to be able to be renewed as quickly as it is consumed.

Unlike materials derived from fossil matter, renewable starting materials contain $^{14}C$ in the same proportions as atmospheric $CO_2$. All carbon samples taken from living organisms (animals or plants) are in fact a mixture of three isotopes: $^{12}C$ (representing about 98.892%), $^{13}C$ (about 1.108%) and $^{14}C$ (trace amounts, $1.2 \times 10^{-10}$%). The $^{14}C/^{12}C$ ratio of living tissue is identical to that of the atmosphere. In the environment, $^{14}C$ exists in two predominant forms: in mineral form, i.e. carbon dioxide ($CO_2$), and in organic form, i.e. carbon integrated into organic molecules.

In a living organism, the $^{14}C/^{12}C$ ratio is kept constant by the metabolism since the carbon is in continual exchange with the environment. Since the proportion of $^{14}C$ in the atmosphere is constant, this is likewise the case in the organism, while it is alive, since it absorbs this $^{14}C$ just as it absorbs $^{12}C$. The mean $^{14}C/^{12}C$ ratio is equal to $1.2 \times 10^{-12}$ for material of renewable origin, whereas a fossil starting material has a zero ratio. Carbon-14 originates from the bombardment of atmospheric nitrogen (14), and oxidizes spontaneously with atmospheric oxygen to give $CO_2$. In human history, the $^{14}CO_2$ level increased following atmospheric nuclear explosions, and has since not stopped decreasing after the halting of these tests.

$^{12}C$ is stable, i.e. the number of $^{12}C$ atoms in a given sample is constant over time. $^{14}C$ is itself radioactive (each gram of carbon of a living being contains enough $^{14}C$ isotope to give 13.6 disintegrations per minute) and the number of such atoms in a sample decreases over time (t) according to the law: $n = n_0 \exp(-at)$, in which:
no is the original number of $^{14}C$ (on the death of the creature, animal or plant),
n is the number of $^{14}C$ atoms remaining after time t,
a is the disintegration constant (or radioactive constant); it is related to the half-life.

The half-life (or period) is the time after which any number of radioactive nuclei or of unstable particles of a given species is reduced by half by disintegration; the half-life $T_{1/2}$ is related to the disintegration constant a by the formula $a \cdot T_{1/2} = \ln 2$. The half-life of $^{14}C$ is 5730 years. In 50 000 years, the $^{14}C$ content is less than 0.2% of the initial content and thus becomes difficult to detect. Petroleum products, natural gas and coal therefore contain no $^{14}C$.

Given the half-life ($T_{1/2}$) of $^{14}C$, the $^{14}C$ content is substantially constant from the extraction of the renewable starting materials up to the manufacture of the "biomaterials" derived from these starting materials, and even up to the end of their use.

The $^{14}C$ content of a material of renewable origin may be measured, for example, according to the following techniques:

by liquid scintillation spectrometry: this method consists in counting the "beta" particles emitted by the disintegration of $^{14}C$. The beta radiation emitted by a sample of known mass (known number of carbon atoms) over a certain period of time is measured. This "radioactivity" is proportional to the number of $^{14}C$ atoms, which may thus be determined. The $^{14}C$ present in the sample emits β rays, which, on contact with the scintillation liquid (scintillant), produces photons. These photons have different energies (between 0 and 156 KeV) and form what is known as a $^{14}C$ spectrum. According to two variants of this method, the analysis relates either to the $CO_2$ produced beforehand by combustion of the carbon sample in a suitable absorbent solution, or to benzene after initial conversion of the carbon sample into benzene;

by mass spectrometry: the sample is reduced to graphite or gaseous $CO_2$, and analysed in a mass spectrometer. This technique uses an accelerator and a mass spectrometer to separate the $^{14}C$ ions from the $^{12}C$ ions and thus to determine the ratio of the two isotopes.

These methods for measuring the $^{14}C$ content of materials are precisely described in the standards ASTM D6866 (especially D6866-06) and in the standards ASTM D7026 (especially 7026-04). These methods compare the data measured on the analysed sample with the data for a reference sample of 100% renewable origin, to give a relative percentage of carbon of renewable origin in the sample.

The measuring method preferentially used is mass spectrometry described in the standard ASTM D6866-06 ("accelerator mass spectroscopy").

In the present invention, the methylmercaptopropionaldehyde and the methionine are at least partly derived from biomass, they contain organic carbon derived from renewable starting materials and are consequently characterized in that they contain $^{14}C$. In particular, at least 25% and preferably at least 50% by mass of the carbons of MMP are of renewable origin and at least 20% and preferably at least 50% by mass of the carbons of methionine are of renewable origin. The MMP and methionine may comprise 100% carbon of renewable origin, when all the starting materials used are of renewable origin.

In accordance with one preferred embodiment of the invention, acrolein was obtained from glycerol. The glycerol is obtained as a by-product of the manufacture of biofuels or soaps or fatty esters or acids or alcohols from oil-yielding plants such as rape seed, sunflower, soybean, oil palm, jatropha or castor, or from animal fat.

In accordance with one embodiment, methyl mercaptan was obtained from hydrogen sulfide $H_2S$ and methanol in the presence of a catalyst according to the reaction:

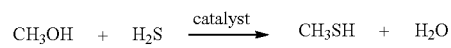

the methanol possibly originating from the pyrolysis of wood or from the fermentation of biomass, for example of plant crops such as wheat, sugarcane or beetroot to give fermentable products.

The methanol may also originate from the gasification of any animal or plant matter leading to a synthesis gas composed essentially of carbon monoxide and hydrogen, which is reacted with water. Non-limiting examples of matter of animal origin include fish oils and fats, such as cod liver oil, whale oil, sperm whale oil, dolphin oil, seal oil, sardine oil, herring oil, shark oil, bovine, pig, goat, horse and poultry oils and fats, such as tallow, lard, milk fat, chicken fat, beef fat, pig fat, horse fat and the like. Examples of matter of plant origin include plant oils, cereal straw fodder, for instance wheat straw or corn straw; cereal residues, for instance corn residues; cereal flours, for instance wheat flour; cereals such as wheat, barley, sorghum, corn; wood, wood waste and rejects; grain; sugarcane, sugarcane residues; pea shoots and stems; beetroot, molasses such as beetroot molasses; potato, potato haulms, potato residues; starch; mixtures of cellulose, hemicellulose and lignin; or papermaking black liquor.

As regards the conversion of synthesis gas into methanol, according to the reaction:

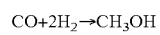

reference may be made to "Procédés de pétrochimie, IFP, ENSPM", 1985, 2nd edition, pp 90-104 and to "Fundamentals of Industrial Catalytic Processes", Wiley, 2nd edition, 6.4.8.

The methanol may also result from the direct (controlled) oxidation of methane produced from biomass:

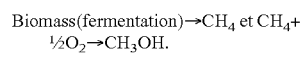

The production of methane from biomass is known. Methane is obtained from biogas. Biogas is gas produced by the fermentation of animal and/or plant organic matter in the absence of oxygen. This fermentation, also known as methanization, takes place naturally or spontaneously in refuse sites containing organic waste, but may be performed in digesters, for example for treating purification sludges, industrial or agricultural organic waste, pig litter or household refuse. Preferably, the biomass used contains animal dejecta serving as a nitrogen input necessary for the growth of microorganisms that ensure fermentation of the biomass to methane. Biogas is composed essentially of methane and carbon dioxide, and the carbon dioxide is then removed by washing the biogas using a basic aqueous solution of sodium hydroxide, potassium hydroxide or amine, or alternatively with water under pressure or by absorption in a solvent such as methanol. According to this route, it is possible to obtain pure methane of consistent quality. Reference may be made to the various methanization techniques of the prior art, to the article "Review of Current Status of Anaerobic Digestion Technology for Treatment of Municipal Solid Waste", November 1998, RISE-AT and to the various biological processes existing for the treatment of waste water, for instance the Laran® process from Linde.

As regards the method for synthesizing methyl mercaptan from methanol, reference may be made, for example, to the method described in patents FR 7 343 539 and FR 2 477 538, which consists in performing the synthesis of MSH by vapour-phase reaction between methanol and $H_2S$ at a temperature, at any point in the reaction mass, of between 280° C. and 450° C. and preferably between 320° C. and 370° C., at a pressure of between 2.5 and 25 bar and preferably between 7 and 12 bar, the reaction being performed by passing the reagents over at least three successive beds of catalyst, all of the $H_2S$ being introduced into the first bed and a fraction of the total methanol being introduced into each bed, the overall mole ratio of $H_2S$ to the total methanol being between 1.10 and 2.5. The catalyst used for this reaction is preferably an activated alumina with a specific surface area of between 100 and 400 m²/g, such as in the form of beads 2 mm to 5 mm in diameter.

According to one embodiment of the invention, methyl mercaptan was obtained by direct reaction of synthesis gas derived from biomass, composed essentially of carbon monoxide and hydrogen, with hydrogen sulfide, according to a catalytic process, and without proceeding via methanol:

$$CO+2H_2+H_2S \rightarrow CH_3SH+H_2O$$

In accordance with one embodiment of the invention, hydrogen cyanide was obtained by reacting ammonia with methane or methanol, optionally in the presence of air and/or oxygen, at least one of the reagents chosen from ammonia, methane and methanol having been obtained from biomass.

The current industrial production of hydrogen cyanide HCN is based mainly on the Andrussow process dating from the 1930s, consisting of an ammoxidation of methane according to which ammonia is reacted with methane in the presence of air and optionally of oxygen over a catalyst composed of rhodanized platinum gauze at a temperature ranging from 1050° C. to 1150° C., according to the reaction:

$$CH_4+NH_3+3/2O_2 \rightarrow HCN+3H_2O+heat$$

Generally, the mole ratio $CH_4/NH_3$ ranges from 1.0 to 1.2 and the mole ratio $(CH_4+NH_3)$/total $O_2$ ranges from 1.6 to 1.9; the pressure is generally from 1 to 2 bar.

Another process (Degussa) for producing HCN is based on the reaction of ammonia with methane, in the absence of oxygen or air, at a temperature of about 1300° C. The reaction is performed in platinum-lined sintered alumina tubes. The bundle of tubes is heated with gas inside an oven.

It is also possible to use methanol in place of methane to produce HCN according to the reaction:

$$CH_3OH+NH_3+O_2 \rightarrow HCN+3H_2O$$

This process, described especially in the 1950-1960s in patents GB 718 112 and GB 913 836 from Distillers Company, uses a catalyst based on molybdenum oxide at a temperature ranging from 340° C. to 450° C., or a catalyst based on antimony and tin at a temperature ranging from 350° C. to 600° C.

Ammonia may be obtained from hydrogen derived from a synthesis gas (composed essentially of carbon monoxide and hydrogen) resulting from the gasification of biomass. Gasification is a thermochemical process for producing a hydrogen-rich gas from biomass and a gaseous reagent such as air, oxygen or steam. The conversion takes place at high temperature (800-1000° C.) and generally at atmospheric pressure or a mild positive pressure. The oxygen concentration (in the air or the water) is not sufficient during the gasification to lead to full oxidation. Thus, large amounts of CO and $H_2$ are produced according to the following reactions:

$$C+H_2O \rightarrow CO+H_2$$

$$C+CO_2 \rightarrow 2CO$$

As biomass, it is possible to use any matter of animal or plant origin already indicated previously.

The hydrogen, after conversion with steam of the carbon monoxide produced from the synthesis gas, is purified before being introduced into a catalytic ammonia synthesis reactor at high pressure (100 to 250 bar).

The hydrogen used to prepare the ammonia may also originate from the recovery of residual liquor from the manufacture of cellulose pulps. Reference may be made to documents FR 2 544 758, EP 666 831 or U.S. Pat. No. 7,294,225 from Chemrec, which describe especially the gasification of residual liquors from cellulose manufacture.

Methane, as already indicated above, may be obtained from biogas ($CH_4/CO_2$) produced by the fermentation of animal or plant organic matter in the absence of oxygen, the $CO_2$ being removed by washing the biogas with an aqueous basic solution of sodium hydroxide, potassium hydroxide or amine, or alternatively with water under pressure or by absorption in a solvent.

Methanol, as already indicated above, may be obtained by fermentation of biomass, or by pyrolysis of wood, or by gasification of any matter of animal or plant origin leading to a synthesis gas composed essentially of carbon monoxide and hydrogen, which is reacted with water, or by direct oxidation of methane produced from biomass.

A subject of the invention is also a process for manufacturing methylmercaptopropionaldehyde, comprising at least the following steps:
  (a) dehydration of glycerol to acrolein starting with an aqueous glycerol solution in the presence of an acidic catalyst,
  (b) purification of the aqueous stream obtained from step (a) to obtain an acrolein stream containing less than 15%, preferably less than 7% and more preferably less than 4% by mass of water relative to the acrolein,
  (c) reaction of the acrolein stream obtained from step (b) with methyl mercaptan in the presence of a catalyst,
  (d) optionally, purification of the product obtained in step (c).

The MMP produced according to the process of the invention after step (c) or (d) may also be subjected to a reaction with hydrogen cyanide or sodium cyanide during a step (e) followed by a subsequent conversion to produce methionine or the hydroxy analogue of methionine, which may then be optionally purified.

The first step (a) of dehydration of glycerol may be performed in the gas phase in a reactor in the presence of a catalyst at a temperature ranging from 150° C. to 500° C. and preferably between 250° C. and 350° C., and a pressure of between $10^5$ and $5 \times 10^5$ Pa.

The dehydration of glycerol may be performed in the liquid phase, and in this case the temperature is between 150° C. and 350° C. at a pressure ranging from $5 \times 10^5$ Pa to $100 \times 10^5$ Pa.

Preferably, the first step is performed in the gas phase.

The reactor used may function as a fixed bed, a fluidized bed, a circulating fluidized bed, or in a modular configuration (plates or baskets), in the presence of solid acidic catalysts.

The catalysts that are suitable for use are homogeneous or multi-phase materials, which are insoluble in the reaction medium and which have a Hammett acidity, noted $H_0$, of less than +2 as indicated in U.S. Pat. No. 5,387,720, which makes reference to the article by K. Tanabe et al. in "Studies in Surface Science and Catalysis", Vol. 51, (1989), chap. 1 and 2; the Hammett acidity is determined by amine titration using indicators or by gas-phase adsorption of a base. The catalysts satisfying the acidity criterion $H_0$ less than +2 may be chosen from natural or synthetic siliceous materials or acidic zeolites; mineral supports, such as oxides, coated with mono-, di-, tri- or polyacidic inorganic acids; oxides or mixed oxides, or alternatively heteropolyacids.

These catalysts may also be formed by a heteropolyacidic salt in which protons of the said heteropolyacid are exchanged with at least one cation chosen from elements belonging to groups I to XVI of the Periodic Table of the Elements, these heteropolyacid salts containing at least one element chosen from the group comprising W, Mo and V.

Among the mixed oxides, mention may also be made of those based on iron and phosphorus and those based on caesium, phosphorus and tungsten.

Advantageously, the catalysts are chosen from zeolites, Nafion® composites (based on sulfonic acid of fluoropolymers), chlorinated aluminas, phosphotungstic and silicotungstic acids and acid salts, and various solids of metal oxide type such as tantalum oxide $Ta_2O_5$, niobium oxide $Nb_2O_5$, alumina $Al_2O_3$, titanium oxide $TiO_2$, zirconium oxide $ZrO_2$, tin oxide $SnO_2$, silica $SiO_2$ or silico-aluminate $SiO_2$—$Al_2O_3$, impregnated with acid functions such as borate $BO_3$, sulfate $SO_4$, tungstate $WO_3$, phosphate $PO_4$, silicate $SiO_2$, or molybdate $MoO_3$. According to the literature data, these catalysts all have a Hammett acidity $H_0$ of less than +2.

The preferred catalysts are sulfated zirconias, phosphated zirconias, tungstated zirconias, siliceous zirconias, titanium oxides or tin oxides, or phosphated or phosphotungstated aluminas or silicas.

The process of the invention generally starts with crude glycerol, i.e. typically containing 80-90% glycerol, 1% to 10% salts, 1% to 4% of non-glycerolic organic matter and 3% to 15% water. The process advantageously starts with desalinated glycerol, which may be obtained from crude glycerol via any means known to those skilled in the art, for instance distillation under reduced pressure or flash distillation under reduced pressure or separation using ion-exchange resins as described, for example, in patent application EP 1 978 009. The process may also start with salt-free glycerol obtained via oil transesterification processes catalysed with heterogeneous catalysts. The process may also start with refined glycerol with a purity of greater than 98%, 99% or 99.5%.

At the reactor entry, a mixture of glycerol and water with a glycerol mass concentration ranging from 20% to 99% and preferably between 30% and 80% is generally used.

The glycerol/water mixture may be used in liquid form or in gaseous form, preferably in the gas-phase form.

One preferred embodiment of the invention consists in sending a mixture containing at least glycerol, water, oxygen or a gas containing oxygen, and, where appropriate, an inert gas and/or recycled gases, in the gas phase, through a bed of a catalytic system as defined previously, maintained at a reaction temperature of between 150 and 500° C.

The amount of oxygen is chosen so as to be outside the flammability domain at any point in the installation. The mole ratio between the molecular oxygen and the glycerol is generally from about 0.1 to 1.5 and preferably from 0.3 to 1.0.

Advantageously, the glycerol dehydration reaction may also be performed in the absence of oxygen, but in the presence of an amount of hydrogen ranging from 0.1% to 10% by volume relative to the reaction mixture, and of a catalyst chosen from those described in patent application US 2008/018 319.

The charge sent into the reactor may be preheated to a preheating temperature of about 150° C. to 350° C.

The process is performed at a pressure of about atmospheric pressure and preferably, more specifically, at a slightly higher pressure.

The contact time expressed in seconds is the ratio between the volume of the bed of catalyst and the volume of the gaseous reagents delivered per second. The average temperature and pressure conditions existing in a bed may vary according to the nature of the catalyst, the nature of the catalytic bed and the dimensions of the catalyst. In general, the contact time is from 0.1 to 20 seconds and preferably from 0.3 to 15 seconds.

After step (a), an aqueous stream is obtained, which may be liquid or gaseous, containing the desired acrolein, water, unreacted glycerol, and by-products such as hydroxypropanone, propanaldehyde, acetaldehyde, formaldehyde, acrylic acid, propionic acid, acetic acid, formic acid, acetone, phenol, adducts of acrolein with glycerol, glycerol polycondensation products, cyclic glycerol ethers, and also light compounds such as nitrogen, oxygen, carbon monoxide and carbon dioxide. Some of these products are heavy compounds, while others are condensable light compounds. For others, they are light compounds that are uncondensable under the temperature and pressure conditions usually employed.

Step (b) in the process according to the invention consists in purifying the said aqueous stream to obtain an acrolein stream containing less than 15%, preferably less than 7% and more preferably less than 4% by mass of water relative to the acrolein, i.e. a water/acrolein mass ratio of less than 0.15, preferably less than 0.07 and more preferably less than 0.04.

According to a first alternative, step (b) consists in purifying the stream containing acrolein, comprising an absorption in water or a recycled aqueous stream to allow the uncondensables to pass through as the head fraction and to recover a dilute aqueous acrolein solution as the tail fraction, followed by a water/acrolein separation by distillation to obtain as the head fraction a gaseous or liquid stream comprising more than 80% by mass of acrolein and less than 15% by mass of water relative to the acrolein, preferably more than 90% by mass of acrolein and less than 7% by mass of water relative to the acrolein, and more preferably more than 95% by mass of acrolein and less than 4% by mass of water relative to the acrolein.

The aqueous stream exiting step (a) may be cooled via one or more heat exchangers.

It is then absorbed in water or a recycled aqueous stream, to form a dilute aqueous acrolein solution, typically containing less than 7% by mass of acrolein. This absorption may be performed in a packed column or a plate column, preferably counter-currentwise. Advantageously, the uncondensable light compounds, such as nitrogen, oxygen, carbon monoxide and carbon dioxide, are removed from the top of the column.

The aqueous acrolein solution is then separated by distillation. To do this, a chain of distillation columns may be used, as described, for example, in U.S. Pat. No. 3,433,840, or a single column, as described, for example, in documents EP 1 300 384 and EP 1 474 374. This distillation makes it possible to recover, on the one hand, a stream formed mainly of water, and, on the other hand, a gaseous or liquid stream with a mass content of acrolein of greater than 75% and a mass content of water of less than 15% relative to the acrolein, and preferably more than 82% by mass of acrolein and less than 7% of water relative to the acrolein, and preferably more than 95% by mass of acrolein and less than 4% of water relative to the acrolein. This final stream is sent towards step (c).

The stream formed mainly of water also contains heavy impurities, with a boiling point higher than that of acrolein. The majority of this aqueous stream is recycled into the absorption step and a small part of this stream is removed, so as to deconcentrate the heavy compounds of the water loop. The light by-products, with a boiling point lower than that of acrolein, for instance acetaldehyde, are either removed as the head fraction in the distillation, or remain in the acrolein stream sent into step (c) and are removed during a step (d) of purification of the MMP. When the light by-products are removed as the head fraction of the distillation column, the gaseous or liquid stream with a mass content of acrolein of greater than 75% and a mass content of water of less than 15% relative to the acrolein, and preferably more than 82% by mass of acrolein and less than 7% of water relative to the acrolein, and preferably more than 95% by mass of acrolein and less than 4% of water relative to the acrolein, may be advantageously recovered by withdrawal at an intermediate plate located between the column feed and the column head, as described, for example, in document EP 1 300 384.

Optionally, when the aqueous stream exiting step (a) is gaseous, the cooling performed on the aqueous stream exiting step (a) may be performed at a temperature such that the acrolein remains predominantly in gaseous form and such that it forms a liquid phase containing part of the water and the majority of the compounds with a boiling point higher than that of water, including, for example, acrylic acid and glycerol. This temperature is typically between 50° C. and 100° C. The liquid phase is then separated from the gas phase containing the majority of the acrolein. This cooling step may also be performed in a packed column or a plate column. A small stream of liquid, for example an aqueous solution, may be injected into the top of this column. A stream of liquid that contains the heavy impurities, for instance glycerol and acrylic acid, is recovered at the bottom of this column. An aqueous gaseous stream containing the majority of the acrolein exits from the top of this column. The gaseous stream containing acrolein is then absorbed in water, as described previously.

According to a second alternative, step (b) consists of a partial purification of the gaseous aqueous stream containing acrolein obtained in step (a), comprising cooling of the said gaseous stream and separation of a liquid stream formed from the majority of the water and acrylic acid, and a gaseous stream that contains less than 15% by mass of water relative to the acrolein, preferably less than 7% of water relative to the acrolein and preferably less than 4% of water relative to the acrolein. It is possible, as described in patent EP 022 697, to perform a first wash of the gaseous aqueous stream exiting step (a) with a small amount of water in a washing column to remove the acrylic acid, followed by cooling of the stream to a temperature generally ranging from 0° C. to 50° C. to condense the aqueous phase, the majority of the acrolein remaining in gaseous form, followed by stripping of the aqueous phase to recover the acrolein entrained into the water.

It is also possible to use a cooling column as described in patent EP 751 110: the gaseous stream exiting step (a) is introduced into the bottom of a column, from which is withdrawn at the bottom a liquid whose temperature is a few degrees below the dew point of the gaseous feed mixture, which liquid is partially cooled and then injected into the top of the column, and the other part of the liquid is sent into a stripping column to recover the acrolein. The gaseous stream obtained at the top of the stripping column is returned into the cooling column with the gaseous feed stream. The gaseous stream exiting at the top of the cooling column is cooled to a temperature generally of 0° C. to 50° C. and condensed liquids are returned into the top of the cooling column.

These two devices make it possible to obtain a gaseous mixture of acrolein, light impurities and uncondensable gases, which contains less than 15% by mass of water relative to the acrolein, preferably less than 7% of water relative to the acrolein and preferably less than 4% of water relative to the acrolein. In so far as the acrolein has not been separated from the uncondensable gases or from the light impurities, the separation of the uncondensables is performed in step (c) and that of the light impurities is performed in step (d).

According to a third alternative, step (b) consists of a purification of the acrolein stream exiting step (a) by distillation. This third alternative is advantageously performed when the stream exiting step (a) contains little uncondensable gas.

The gaseous stream exiting step (a) is partially cooled using one or more heat exchangers. It is then injected into a distillation column that comprises a condenser for cooling the stream exiting from the top of the distillation column to a temperature of $-10°$ C. to $20°$ C. at a pressure of 1 to 3 bar and a reboiler for providing a bottom temperature of 100° C. to 130° C. The reflux level of the column is advantageously from 2 to 30. A stream formed from water and heavy impurities is recovered at the bottom. At the exit of the head condenser, a gas phase formed from uncondensables (nitrogen, oxygen, carbon dioxide, carbon monoxide) is recovered, and removed, and a liquid phase formed from more than 75% by mass of acrolein and less than 15% by mass of water relative to the acrolein, preferably more than 82% by mass of acrolein and less than 7% of water relative to the acrolein and more preferentially more than 95% by mass of acrolein and less than 4% of water relative to the acrolein is recovered. The majority of this liquid phase is returned into the column for refluxing and partly withdrawn to feed step (c). Alternatively, the head condenser of the distillation column can function at a higher temperature, from 30° C. to 80° C.: in this case, the liquid stream exiting the condenser is returned into the column for refluxing, and the gaseous stream, which comprises the acrolein and the uncondensables, is cooled in a second condenser functioning at a temperature of $-10°$ C. to $+20°$ C. so as to recover a gas phase formed from uncondensables (nitrogen, oxygen, carbon dioxide, carbon monoxide), which is removed, and a liquid phase formed from more than 75% by mass of acrolein and less than 15% by mass of water relative to the acrolein, preferably more than 82% by mass of acrolein and less than 7% of water relative to the acrolein and more preferentially more than 95% by mass of acrolein and less than 4% of water relative to the acrolein. Optionally, the liquid phase may undergo an additional rectification to reduce its water content, and/or topping to reduce its light-fraction content.

Step (c) in the process according to the invention consists in reacting the liquid or gaseous acrolein stream obtained in step (b) with methyl mercaptan in the presence of a catalyst. The reaction is performed in the liquid phase in the presence of a basic catalyst, generally in the absence of solvent, at a temperature preferably ranging from 20° C. to 60° C., with a slight excess of MSH. Examples of catalysts that may be used include organic bases, optionally combined with an organic acid. Examples that may be mentioned include organic bases selected from amines such as those described in patent application WO 96/40631, organic bases of N-alkylmorpholine type described in document EP 1 556 343, or systems formed from a basic compound and an acidic compound in mole ratios of less than 0.3/1, described in document EP 1 408 029. Preferably, pyridine combined with acetic acid is used as catalyst.

This reaction may be performed in various ways, in batch or continuous mode. The liquid or gaseous acrolein and methyl mercaptan are introduced simultaneously (temporarily or spatially) or successively into the reactor or the reaction column. Advantageously, they are introduced onto a feedstock of MMP originating from a preceding batch or onto a stream of recycled MMP if the reaction is performed continuously. Many processes have been described and may be used for performing this step (c).

As a result of the purification of the acrolein stream used to perform the reaction with methyl mercaptan, it is possible to obtain high yields of MMP, generally higher than those obtained with a direct process for manufacturing MMP from glycerol.

The MMP thus obtained may be used in this form or purified in a step (d), for example by distillation. Light impurities and heavy sulfur products are thus separated out, and then incinerated.

The reaction of MMP, optionally purified, with hydrogen cyanide or sodium cyanide is performed under conditions well known to those skilled in the art, according to the Bücherer or Strecker synthesis, to give either methionine or the hydroxy analogue of methionine, after conversion of the reaction product, as described in document "Techniques de l'Ingénieur, Traité Génie des procédés", J 6 410-1 to 9.

According to one preferred embodiment of the process according to the invention, step (e) is performed by reacting MMP with hydrogen cyanide in the presence of ammonium carbonate to form a hydantoin compound, followed by saponification with potassium hydrogen carbonate or potassium carbonate, leading to potassium methioninate, which, after acidification with carbonic acid, leads to D,L-methionine, which crystallizes.

According to another embodiment of the process according to the invention, step (e) is performed by reacting MMP with HCN under pyridine catalysis or a combination of pyridine and acetic acid, leading to a cyanohydrin compound, which is then hydrolysed in sulfuric acid medium in two successive steps using a first low temperature (about 50° C.) and a second higher temperature (about 100° C.). The hydroxy analogue of methionine is then isolated either by extraction, for example with a solvent such as methyl isobutyl ketone or methyl ethyl ketone, or by acidification with sulfuric acid, followed by decantation to remove the ammonium sulfate, followed by crystallization of the hydroxy analogue of methionine.

The methionine (or the hydroxy analogue of methionine) obtained according to the process of the invention is used for preparing compositions for poultry feed or animal feed.

The invention is described in greater detail with reference to the following examples, which are given for purely illustrative purposes and are in no way limiting.

EXAMPLES

Example 1

An aqueous solution containing 20% by mass of glycerol (742 g/h) is vaporized by passing it through an exchanger with a skin temperature of 350° C., and then injected at atmospheric pressure together with a stream of air at a flow rate of 100 normal liters per hour onto a tubular fixed-bed reactor with an inside diameter of 30 mm, maintained at 320° C. and containing 537 g of tungstated zirconia (batch Z1044 Dai Ichi Kigenso).

The absorbed hot gases are sent to an absorption column, into which are injected 742 g/h of water at the top with recirculation and comprising an external exchanger such that the column head temperature is 20° C. The liquid stream containing about 5% acrolein is then injected into a distillation tower functioning at atmospheric pressure. The vapour phase is condensed and 87 g/h of a liquid containing about 85% acrolein, 2.4% formaldehyde, 8% acetaldehyde, 1.2% propionaldehyde, 0.2% acetone, 0.2% allylic alcohol and 3% water is recovered.

A 50 g feedstock of MMP is introduced into a 500 mL reactor, followed by 1.7 g of a mixture of pyridine at 48% by mass in acetic acid. At a reaction temperature of 60° C., 200 g of the 85% acrolein solution obtained above and 149.8 g of 99.5% methyl mercaptan are simultaneously introduced over a period of 30 minutes with stirring, and the mixture is then left to react for a further 10 minutes at this temperature, before rectifying it under reduced pressure at 15 mmHg. A 353 g fraction boiling at about 65° C. of MMP with an estimated purity of 99% is recovered. The acetaldehyde, propionaldehyde, acetone and allylic alcohol are distilled off at lower temperature. The chemical yield for the conversion of the glycerol into MMP is 78%. By using methyl mercaptan derived from biomass, it is possible to obtain MMP containing 100% of renewable carbon.

Example 2

860 g of aqueous ammonium carbonate solution containing 7.8% ammonia and 12.4% carbon dioxide are introduced into a closed reactor. After heating to 90° C. with vigorous stirring, 105 g of the MMP produced in Example 1 and 28.5 g of hydrogen cyanide are gradually injected. The mixture is then maintained at 110° C. for 1 hour. The reactor is cooled to 80° C. and then degassed slowly so as to bring the mixture containing the 5-(2-methylmercaptoethyl)hydantoin to atmospheric pressure. 900 g of 40% potassium hydrogen carbonate solution are added and the mixture is maintained at 180° C. under 8 bar for 20 minutes. The mixture is then gradually depressurized to atmospheric pressure and part of the water is evaporated off so that the mixture contains about 20% potassium methioninate. It is then cooled to about 25° C. and carbon dioxide is injected at a pressure of 2-3 bar so as to lower the pH to 5.6. A suspension is obtained, which is filtered off. The recovered solid is washed and then dried. 98 g of D,L-methionine are recovered. The filtrate is recovered and concentrated, and may be recycled into the solution containing the 5-(2-methylmercaptoethyl)hydantoin.

Example 3

420 g of MMP produced in Example 1 and 1.7 g of a mixture of pyridine at 48% in acetic acid are introduced into a stirred reactor. 111 g of hydrogen cyanide are injected over a period of 45 minutes, while keeping the temperature between 35° C. and 40° C., followed by heating for 30 minutes at 45° C. The mixture obtained, consisting mainly of 2-hydroxy-4-(methylthio)butyric acid, is added over a period of 45 minutes at 60° C. to 591 g of an aqueous solution containing 66% sulfuric acid. The mixture is stirred for 10 minutes at 65° C., 380 g of hot water at 80° C. are then added and this mixture is stirred for 2 hours at 90° C. The reaction mixture is then extracted with 1480 g of methyl isobutyl ketone. The upper phase is then evaporated off at 70° C. under vacuum to give 637 g of 2-hydroxy-4-(methylthio)butyric acid at 88% in water (hydroxy analogue of methionine).

Example 4

An aqueous solution containing 33% glycerol (450 g/h) is vaporized by passing it through an exchanger with a skin temperature of 350° C., and then injected at atmospheric pressure together with a stream of air of 100 normal liters per hour and a stream of carbon dioxide of 50 normal liters per hour onto a tubular fixed-bed reactor with an inside diameter of 30 mm maintained at 320° C. and containing 537 g of tungstated zirconia (batch Z1044 Dai Ichi Kigenso).

The hot gases are sent into the bottom of a cooling column similar to that described in patent EP 751 110, with external cooling by recirculation. The bottom temperature is 65° C. The aqueous tail solution is brought to 90° C. and stripped with a gentle stream of nitrogen so as to obtain at the bottom an aqueous solution containing 150 ppm of acrolein. The gases obtained from this stripping (comprising nitrogen, acrolein and water) are sent to the cooling column.

The gases exiting from the top of the cooling column, comprising 16 mol % of acrolein, 1.5 mol % of water (i.e. a water/acrolein mass ratio of 0.035) in a mixture of nitrogen, $CO_2$, CO, acetaldehyde and $O_2$ are sent into the bottom of an absorption column fed at the top with MMP cooled to $-10°$ C. The column tail fraction is sent into a continuous stirred reactor, into which are injected 64.5 g/h of methyl mercaptan and 0.8 g/h of a mixture of pyridine at 48% by mass in acetic acid. The reaction is performed in the liquid phase. The MMP produced is rectified under reduced pressure at 15 mmHg and a fraction boiling at about 65° C. is recovered.

The chemical yield for the conversion of the glycerol into MMP is 76%.

Example 5

An aqueous solution containing 25% glycerol (742 g/h) is vaporized by passing it through an exchanger with a skin temperature of 350° C., and then injected at 2.8 bar absolute together with an oxygen stream of 10 normal liters per hour onto a tubular fixed-bed reactor with an inside diameter of 30 mm maintained at 320° C. and containing 500 g of tungstated zirconia (batch Z1044 Dai Ichi Kigenso).

The hot gases leaving the reactor are cooled to 150° C. and then sent into the upper third of a 10-plate distillation column comprising a condensing head cooling to 67° C. at 2 bar absolute. At the bottom of this column, a 630 g/h stream containing water and the heavy impurities is recovered. At the exit of the head condenser, a liquid phase (1540 g/h) is recovered and reinjected entirely into the column, and a gaseous stream is recovered. The said gaseous stream is cooled to 5° C. via a second condenser, which allows the uncondensables (CO, $CO_2$ and $O_2$) to escape and allows recovery of 108 g/h of a liquid containing 83% acrolein and 5.5% water.

This acrolein stream, and a stream of 80 g/h of methyl mercaptan and 0.8 g/h of a mixture of pyridine at 10% by mass in acetic acid, are injected into a packed column cooled to 30° C. and equipped with recirculation of part of the liquid leaving from the bottom into the top. The upper part of the liquid leaving from the bottom is then topped, and rectified under reduced pressure at 15 mmHg to recover a fraction boiling at about 65° C., formed from MMP with a purity of 98%.

The chemical yield for the conversion of the glycerol to MMP is 75%.

Example 6

Comparative

An aqueous solution containing 20% by mass of glycerol (742 g/h) is vaporized by passing it through an exchanger with a skin temperature of 350° C., and then injected at atmospheric pressure together with a stream of air at a flow rate of 100 normal liters per hour onto a tubular fixed-bed reactor with an inside diameter of 30 mm, maintained at 320° C. and containing 537 g of tungstated zirconia (batch Z1044 Dai Ichi Kigenso).

The absorbed hot gases are sent to an absorption column, in which are injected 742 g/h of water at the top with recirculation and comprising an external exchanger such that the column head temperature is 20° C. The liquid stream containing about 5% acrolein is then injected into a distillation tower functioning at atmospheric pressure comprising fewer plates than in Example 1. The vapour phase is condensed and 101 g/h of a liquid containing about 73.5% acrolein, 2.0% formaldehyde, 6.9% acetaldehyde, 1.0% propionaldehyde, 0.2% acetone, 0.2% allyl alcohol and 16.2% water are recovered, i.e. a water content of 22% by mass relative to the acrolein.

A 50 g feedstock of MMP is introduced into a 500 mL reactor, followed by 1.7 g of a mixture of pyridine at 48% by mass in acetic acid. At a reaction temperature of 60° C., 200 g of the 73.5% acrolein solution obtained above and 139 g of 99.5% methyl mercaptan are simultaneously introduced over a period of 30 minutes with stirring, and the mixture is then left to react for a further 10 minutes at this temperature, before rectifying it under reduced pressure at 15 mmHg. A fraction boiling at about 65° C. of 161 g of MMP with an estimated purity of 98% is recovered. The chemical yield for the conversion of the glycerol into MMP is 33%.

The invention claimed is:

1. A process for manufacturing an amount of methylmercaptopropionaldehyde which comprises
    adding methyl mercaptan to an acrolein stream containing less than 7% by mass of water relative to the acrolein, wherein at least one from among the acrolein and the methyl mercaptan employed in this reaction is obtained from a biomass.

2. A process for manufacturing methionine or the hydroxy analogue of methionine which comprises
    reacting hydrogen cyanide or the sodium salt of hydrogen cyanide with the amount of methylmercaptopropionaldehyde made by the method of claim 1.

3. The process according to claim 1, wherein the acrolein stream is obtained by dehydrating glycerol.

4. The process according to claim 1, wherein the methyl mercaptan is obtained by reacting hydrogen sulfide with methanol, the methanol having been obtained from the biomass (i) by hydrolysis of wood or by fermentation of the biomass, (ii) by gasification of any matter of animal or plant origin leading to a synthesis gas composed essentially of carbon monoxide and hydrogen, which is reacted with water, or (iii) by direct oxidation of methane produced from the biomass.

5. The process according to claim 1, wherein the methyl mercaptan is obtained from the biomass by direct reaction of synthesis gas $CO/H_2$ derived from the biomass with hydrogen sulfide.

6. The process according to claim 2, wherein the hydrogen cyanide is obtained by reacting ammonia with methane or methanol, optionally in the presence of air and/or oxygen, wherein at least one of the reagents chosen from ammonia, methane, and methanol having been obtained from the biomass.

7. The process according to claim 6, wherein the ammonia is obtained from hydrogen derived from a synthesis gas $CO/H_2$ resulting from the gasification of the biomass.

8. The process according to claim 6, wherein the methane is obtained from $CH_4/CO_2$ produced by fermentation of animal or plant organic matter in the absence of oxygen, the $CO_2$ being removed by washing the biogas using a basic aqueous solution of sodium hydroxide, potassium hydroxide or amine, or alternatively with water under pressure or by absorption in a solvent.

9. The process according to claim 6, wherein the methanol is obtained by fermentation of the biomass, or by hydrolysis of wood, or by gasification of any matter of animal or plant origin leading to a synthesis gas composed essentially of carbon monoxide and hydrogen, which is reacted with water, or by direct oxidation of methane produced from the biomass.

10. The process according to claim 1, comprising at least the following steps:
(a) dehydration of glycerol to acrolein using an aqueous glycerol solution in the presence of an acidic catalyst,
(b) purification of the aqueous stream obtained from step (a) to obtain the acrolein stream,
(c) reaction of the acrolein stream obtained in step (b) with methyl mercaptan in the presence of a catalyst,
(d) optionally, purification of the product obtained in step (c).

11. The process according to claim 10, and further comprising the following steps:
(e) reaction of the product obtained in step (c) or (d) with hydrogen cyanide or sodium cyanide,
(f) conversion of the product obtained in (e) into methionine or the hydroxy analogue of methionine, and purification thereof.

12. The process according to claim 10, wherein step (b) comprises an absorption in water or a recycled aqueous stream, to allow departure as a head fraction of the uncondensables and to recover as a tail fraction a dilute aqueous acrolein solution, followed by a water/acrolein separation by distillation to obtain as the head fraction a gaseous or liquid stream comprising more than 80% by mass of acrolein and less than 7% by mass of water relative to the acrolein.

13. The process according to claim 10, wherein step (b) consists of partially purifying the gaseous aqueous stream containing acrolein obtained in step (a), and cooling the gaseous stream and separating the liquid stream formed from the majority of the water and acrylic acid, wherein the gaseous stream less than 7% by mass water relative to the acrolein.

14. The process according to claim 10, wherein step (b) consists of purifying the acrolein stream exiting step (a) by distillation.

15. The process according to claim 10, wherein step (c) is performed in the liquid phase in the presence of a basic catalyst, in the absence of solvent, at a temperature preferably ranging from 20° C. to 60° C., with a slight excess of methyl mercaptan (MSH).

16. The process according to claim 10, wherein the chemical yield for the conversion of the glycerol to the methylmercaptopropionaldehyde is 75-78%.

17. The process according to claim 1, wherein the acrolein stream contains less than 4% by mass of the water relative to the acrolein.

* * * * *